(12) United States Patent
Jones (10) Patent No.: US 7,195,921 B2
(45) Date of Patent: *Mar. 27, 2007

(54) ADHERED MEMBRANES RETAINING POROSITY AND BIOLOGICAL ACTIVITY

(75) Inventor: Ronald M. Jones, Mountain View, CA (US)

(73) Assignee: Cholestech Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/816,557

(22) Filed: Apr. 1, 2004

(65) Prior Publication Data

US 2004/0235182 A1    Nov. 25, 2004

Related U.S. Application Data

(60) Provisional application No. 60/460,079, filed on Apr. 2, 2003.

(51) Int. Cl.
*G01N 33/92* (2006.01)
*G01N 33/49* (2006.01)

(52) U.S. Cl. .................. 436/71; 436/63; 436/169; 436/170; 422/56; 422/58

(58) Field of Classification Search .............. 436/63, 436/71, 149, 150, 164, 169, 170; 422/55, 422/56, 58
See application file for complete search history.

(56) References Cited

U.S. PATENT DOCUMENTS

| 4,623,628 | A | 11/1986 | Maaskant et al. |
|---|---|---|---|
| 4,814,077 | A | 3/1989 | Furuyoshi et al. |
| 4,959,324 | A | 9/1990 | Ramel et al. |
| 4,999,287 | A | 3/1991 | Allen et al. |
| 5,087,556 | A | 2/1992 | Ertinghausen |
| 5,114,350 | A | * 5/1992 | Hewett .................. 435/286.4 |
| 5,130,231 | A | 7/1992 | Kennedy et al. |
| 5,135,716 | A | 8/1992 | Thakore |
| 5,213,964 | A | 5/1993 | Jones |
| 5,213,965 | A | 5/1993 | Jones |
| 5,215,886 | A | 6/1993 | Patel et al. |
| 5,401,466 | A | 3/1995 | Foltz et al. |
| 5,409,664 | A | 4/1995 | Allen |

(Continued)

FOREIGN PATENT DOCUMENTS

EP    0 408 223 A1    1/1991

(Continued)

OTHER PUBLICATIONS

International Search report from PCT/US2004/010001 dated Aug. 16, 2004.

*Primary Examiner*—Maureen M. Wallenhorst
(74) *Attorney, Agent, or Firm*—Jacqueline F. Mahoney; Perkins Coie LLP (57) ABSTRACT

An assay pad for measuring the concentration of HDL-associated cholesterol in a sample, a method for using the pad, and a diagnostic assay device for carrying out the method are described. The assay pad includes a polymer adhesive or heat laminate bond. The assay design prevents interference by reagents used for such removal with the HDL quantification reaction or with other assays carried out on the same sample. If desired, removal of non-HDL lipoproteins and assay of HDL cholesterol can be carried out without interruption of the assay.

37 Claims, 3 Drawing Sheets

U.S. PATENT DOCUMENTS

| | | |
|---|---|---|
| 5,417,863 A | 5/1995 | Varady et al. |
| 5,426,030 A | 6/1995 | Rittersdorf et al. |
| 5,451,370 A | 9/1995 | Jones |
| 5,460,974 A | 10/1995 | Kozak et al. |
| 5,496,637 A | 3/1996 | Parham et al. |
| 5,543,054 A | 8/1996 | Charkoudian et al. |
| 5,580,743 A | 12/1996 | Rittersdorf et al. |
| 5,633,168 A | 5/1997 | Glasscock et al. |
| 5,695,947 A | 12/1997 | Guo et al. |
| 5,728,352 A | 3/1998 | Poto et al. |
| 5,786,164 A | 7/1998 | Rittersdorf et al. |
| 5,788,942 A * | 8/1998 | Kitani et al. ............... 422/56 |
| 6,156,492 A | 12/2000 | Kobayashi et al. |
| 6,159,424 A | 12/2000 | Kauhaniemi et al. |
| 6,210,907 B1 | 4/2001 | Cha |
| 6,596,112 B1 * | 7/2003 | Ditter et al. ............... 156/182 |
| 6,881,581 B2 * | 4/2005 | Jones et al. ............... 436/71 |
| 2003/0166291 A1 * | 9/2003 | Jones et al. ............... 436/71 |
| 2003/0175153 A1 | 9/2003 | Anaokar et al. |
| 2003/0224471 A1 * | 12/2003 | Jones et al. ............... 435/11 |
| 2004/0023400 A1 | 2/2004 | Tamura et al. |
| 2005/0124019 A1 * | 6/2005 | Jones ............... 435/11 |
| 2005/0208609 A1 * | 9/2005 | Jones et al. ............... 435/11 |

FOREIGN PATENT DOCUMENTS

| | | |
|---|---|---|
| EP | 0 415 298 B1 | 3/1991 |
| EP | 1 029 928 A2 | 1/2000 |
| EP | 1 357 383 A1 | 10/2003 |
| WO | WO96/15453 A1 | 5/1996 |
| WO | WO 99/58966 A1 | 11/1999 |
| WO | WO 02/02796 A2 | 1/2002 |

* cited by examiner

US 7,195,921 B2

ADHERED MEMBRANES RETAINING POROSITY AND BIOLOGICAL ACTIVITY

This application claims benefit of priority to U.S. Provisional Application No. 60/460,079, filed Apr. 2, 2003.

FIELD OF THE INVENTION

The present invention relates to a high density lipoprotein (HDL)-associated cholesterol assay pad, a method for using said pad, and a diagnostic assay device for carrying out the method.

BACKGROUND OF THE INVENTION

The amount of cholesterol present in the blood is known to be related to the risk of coronary artery disease. Cholesterol circulates in the blood predominantly in protein-bound form. The proteins which transport cholesterol are the lipoproteins, which are subdivided into three classes based on their density. The very-low density lipoproteins (VLDL) are triglyceride-rich lipoproteins which are synthesized in the liver and ultimately converted to low-density lipoproteins (LDL), which transport most of the plasma cholesterol in humans. The high-density lipoproteins (HDL) are lipoproteins which are involved in the catabolism of triglyceride-rich lipoproteins, and in the removal of cholesterol from peripheral tissues and transport to the liver. An inverse relationship between serum HDL levels and risk of coronary disease has been established. In particular, if the proportion of serum cholesterol associated with HDL is low, the risk of coronary disease is increased.

In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

One method for specific HDL cholesterol testing is based on the selective precipitation of non-HDL lipoproteins in serum by a polyanionic compound, such as dextran sulfate, heparin, or phosphotungstate, typically in the presence of a group II cation, such as $Mg^{2+}$, $Mn^{2+}$, or $Ca^{2+}$. The specificity and degree of precipitation are dependent on a variety of factors, including the type and concentration of the precipitating reagent. In general, the order of precipitation of serum cholesterol particles, with increasing concentration of polyanion, is VLDL, LDL, and HDL. HDL usually remains soluble at concentrations of heparin or dextran sulfate which completely precipitate lower density particles, although minor apoE species of HDL may be co-precipitated with lower density particles. By selective precipitation of lower density particles, HDL serum cholesterol levels can be determined.

In a typical lipid assay procedure, a small volume of blood is drawn and centrifuged to produce a clear plasma or serum sample fluid. The sample fluid is then aliquoted into several assay tubes, for determination of (a) total serum cholesterol, (b) triglycerides, and (c) HDL cholesterol. The HDL sample is precipitated, as above, and the lower density particles are removed by filtration or centrifugation prior to cholesterol detection. The samples are then reacted with an enzyme mix containing cholesterol esterase, cholesterol oxidase, peroxidase, and a dye which can be oxidized to a distinctly colored product in the presence of $H_2O_2$. The tubes may be read spectrophotometrically, and the desired total, HDL and LDL cholesterol values determined.

Despite the accuracy and reliability which can be achieved with the liquid-phase cholesterol assay just described, the assay has a number of limitations for use in widespread screening. First, the method uses a venous blood sample, requiring a trained technician to draw and fractionate the blood sample, and aliquot the treated blood to individual assay tubes. At least one of the sample tubes (for HDL determination) must be treated with a precipitating agent and further processed to remove precipitated material. Although some of these procedures can be automated, analytical machines designed for this purpose are expensive and not widely available outside of large hospitals.

Co-owned U.S. Pat. Nos. 5,213,964, 5,213,965, 5,316,196 and 5,451,370, each of which is incorporated herein by reference, disclose methods and assay devices which substantially overcome many of the above-mentioned problems associated with liquid-assay procedures for measuring serum cholesterol levels. In one embodiment, the device is designed for measuring the concentration of HDL-associated cholesterol in a blood sample also containing LDL and VLDL particles. The device includes a sieving matrix capable of separating soluble and precipitated lipoproteins as a fluid sample migrates through the matrix. A reservoir associated with the matrix is designed to release a soluble precipitating agent, for selectively precipitating LDL and VLDL, as fluid sample is drawn into and through the matrix. This allows HDL separation from the precipitated lipoproteins, based on faster HDL migration through the sieving matrix. The fluid sample, thus depleted of non-HDL lipoproteins, then is transferred to a test surface where it is assayed for cholesterol.

The above-referenced devices, while representing an advance over liquid-phase assays, present the possibility of contamination of the flow transport path with the precipitating reagents. Such reagents could interfere with HDL quantification, or with other assay chemistry taking place on other regions of a multi-assay device. The present invention addresses and overcomes these problems.

Further methods and devices for measuring HDL cholesterol in blood samples are disclosed in EP 0408223 and EP 0415298 (Rittersdorf et al.), which describe a continuous assay method carried out on a test strip comprising the following steps and corresponding elements. The blood sample is applied to a separation layer for separating cellular blood constituents. Driven by capillary forces or gravity, the sample flows through a further carrier containing soluble precipitating agents, which, after dissolving in the serum sample, precipitate non-HDL lipoproteins contained in the sample. In a further carrier, the precipitated constituents, above, are filtered from the serum sample to prevent their interference with later HDL quantification. In the same carrier, the sample is transported to a position adjacent the HDL-quantification carrier, and is stored until the HDL quantification step is to be started. Finally, the sample is transferred to an HDL quantification layer, where HDL cholesterol in the serum sample is quantified by an enzymatic reaction.

A disadvantage of this assay design is that the carrier functioning as a reservoir allows migration of the precipitated constituents or soluble reagents into the sample, which can interfere with HDL quantification. In addition, during the storage of the serum sample, HDL can be trapped by adhering to the carrier fibers, precipitating reagents can cause further undesired reactions, and the carrier can become clogged by the drying serum sample.

U.S. Pat. No. 5,135,716 (Thakore) discloses additional devices and methods for HDL quantification in a blood fluid sample. In these devices, the fluid sample flows continuously, though an unbroken path, from an inlet well to a carrier for HDL quantification. Accordingly, the ability to control sample volume entering the HDL test carrier, and to control environmental conditions for the HDL assay, is limited. Nor do the devices provide for simultaneous assay of various analytes from a single fluid sample.

It is therefore the object of the present invention to provide a HDL assay device which overcomes the above-noted prior art disadvantages.

SUMMARY OF THE INVENTION

In one aspect, the invention includes an assay pad formed by joining a HDL test pad and a reagent pad where the assay pad retains porosity sufficient for the sample to pass through the reagent pad to the HDL test pad. The assay pad further retains the biological activity of the reagents on the reagent pad and HDL test pad.

In another aspect, the invention includes an assay device and method for using the device for measuring serum cholesterol associated with high-density lipoproteins (HDL) in a blood fluid sample containing lipoproteins other than HDLs. The device includes a sample distribution array, a HDL test pad in which HDL concentration can be assayed; and a reagent pad containing a binding reagent effective to selectively bind and remove non-HDLs from the fluid sample. The HDL test pad and reagent pad are joined by an adhesive layer or by heating the pads.

In yet another aspect, the invention provides methods of preparing the joined HDL test pad and reagent pad.

DETAILED DESCRIPTION OF THE INVENTION

I. Definitions

The terms below have the following meanings unless indicated otherwise.

An element is in "fluid communication" with another element when a fluid is able to travel from one element to the other via capillary action and/or gravity. The elements do not need to be in direct contact; i.e., other elements through which said fluid can pass may be intervening.

A "pad", as used in the context of a "sample distribution pad", "test pad", "HDL test pad", and "reagent pad" intends a thin, flat mat or cushion, or a piece of absorbent material. Pads may be comprised of any material, such as a porous membrane or fibrous strip, which can contain impregnated or immobilized reagents and through which fluid can move via capillary action and/or gravity.

II. Assay Device

Figure 1:
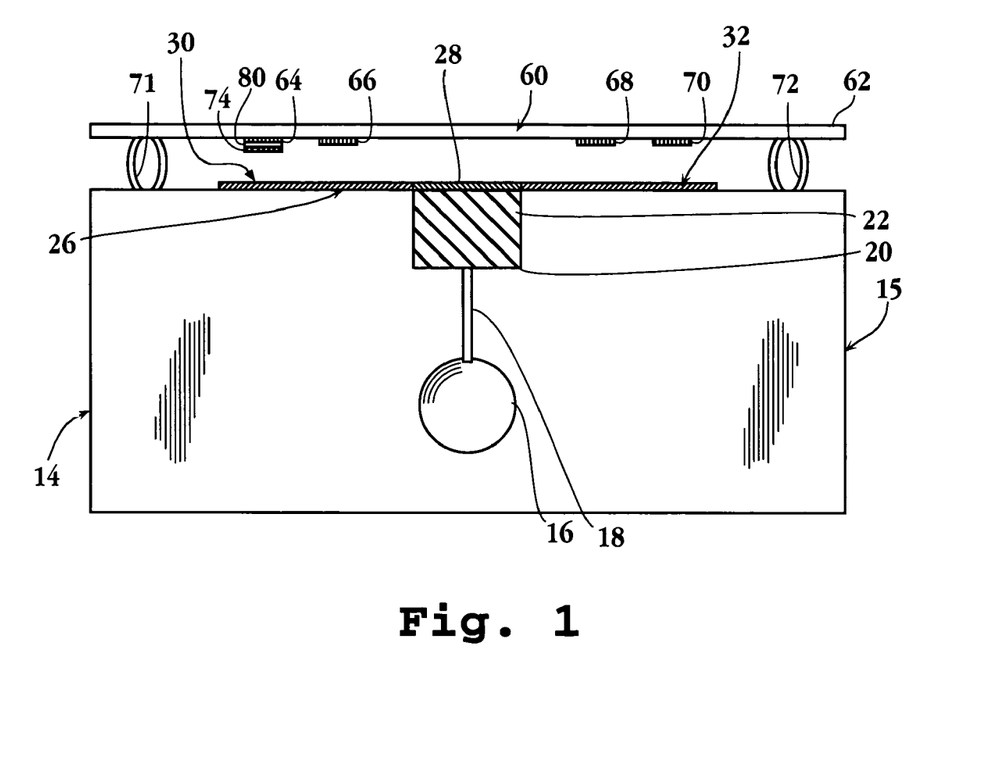
FIG. 1 is a side view of one embodiment of the multi-analyte assay device.
Figure 2:
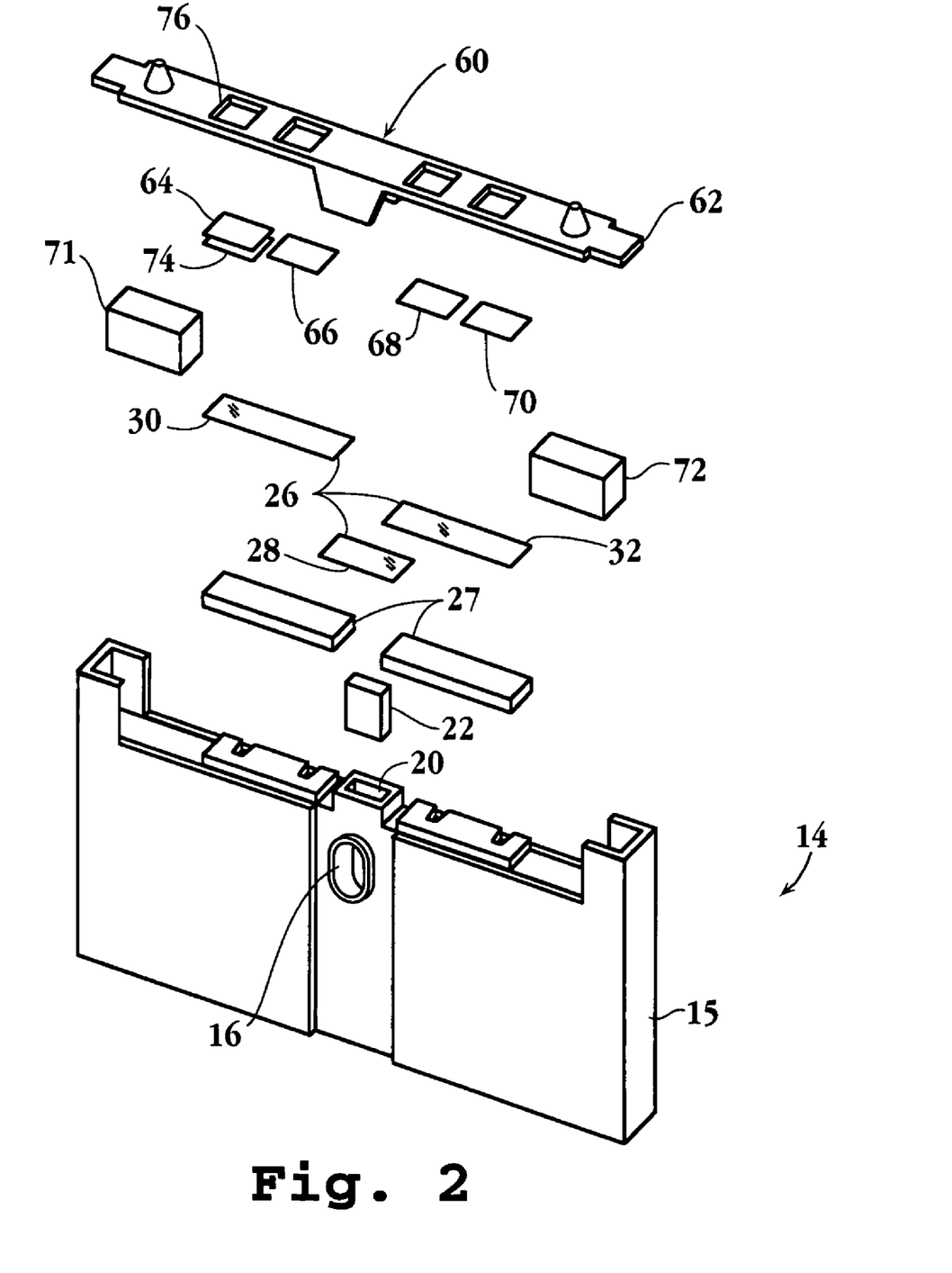
FIG. 2 is a perspective view, in exploded form, of a multi-analyte assay device constructed in accordance with one embodiment of the invention.
Figure 3:
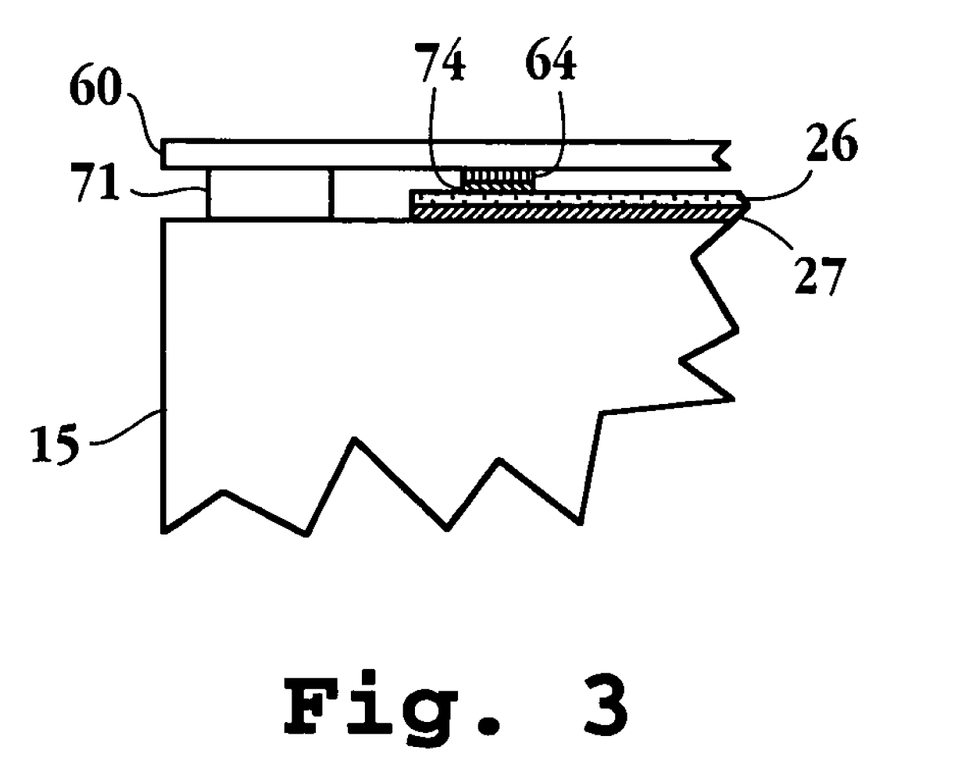
FIG. 3 is a partial side view of the multi-analyte assay device in accord with one embodiment of the invention.

The device in accord with the invention is illustrated in FIGS. 1–3, which will be discussed below. For convenience, similar element numbering is retained in all FIGS. 1–3 to identify like structural features. The device is designed particularly for determining serum cholesterol associated with HDL (also referred to as HDL-associated cholesterol or simply HDL cholesterol) using a small volume of blood or serum sample, typically between 10–50 µL. Other assays, such as total cholesterol, triglyceride, glucose, alanine aminotransferase level (ALT), aspartate amino transferase (AST), Blood Urea Nitrogen (BUN), or creatinine can be determined simultaneously from the same sample. Determination of HDL-associated cholesterol may also be referred to simply as determination of HDL or an HDL assay.

With initial reference to FIGS. 1–3, various embodiments of the multiple-analyte assay device are illustrated, with FIG. 2 shown in exploded format. As best seen in FIG. 1, the multiple-analyte assay device 14 includes a main body or support 15 which defines a well 16 dimensioned and sized to receive a quantity of a blood sample, typically between about 25–50 µL. The well may be in fluid contact with an optional sieving pad 22, which may be carried in a notched region 20 formed in the upper edge of the support. The fluid contact may be direct, or as in the device shown in FIG. 1, provided by a capillary conduit 18 formed in the plate at the base of the well. The support is preferably a plastic plate, with the well, notched region and/or capillary formed by standard molding or machining methods.

Sieving pad 22 carried in region 20 functions to partially remove large particulate matter (including blood cells) as the sample migrates through the pad matrix in a bottom-to-top direction as shown in the figure. Pad 22 is preferably formed of a glass fibrous matrix of material designed to draw aqueous fluid by surface wetting, and to retard the movement of blood cells as the blood sample is drawn through the matrix. One exemplary pad is a glass fiber filter, such as a GF/D, PD008, or F145-02 filter available from Whatman, having a packing density of about 0.16 g/cm$^3$, and a thickness of about 1 mm. The pad is dimensioned to absorb a defined volume of sample fluid, preferably between about 15–25 µL. Sieving pad 22 may additionally contain red blood cell capture reagents, such as lectins, antibodies specific for red blood cell surface membrane proteins, thrombin, or ion exchange agents. In one embodiment, the pad may contain reagents for removal of non-HDL lipoproteins, as described further below.

The sample contacts an elongate strip or sample distribution array 26. The sieving pad 22 may be in fluid contact with array 26 between the well 16 and the array 26. In a preferred embodiment, array 26 is formed of three or more separate membranes in fluid communication. In an embodiment where array 26 is formed of three membranes in fluid communication, as seen in FIG. 2, central sample-application membrane 28 distributes sample fluid to sample-collection membranes 30 and 32. The array 26 may further comprise one or more reagent membranes, not shown, disposed between sample-application membrane 28 and sample-collection membrane 30. The reagent membrane may contain one or more reagents. In one embodiment, the reagent membrane may contain one or more reagents for selectively removing LDL and VLDL as described further below. In another embodiment, reagent membrane may function as a wick to draw sample for multiple tests. Array 26 may also be supported by foam cushions 27 or other supports, as shown in FIG. 2. Array 26 is preferably multiple membranes formed of a matrix of glass fibers. The packing density and thickness of the matrix are such as to absorb and distribute volumes of sample fluid, e.g., 10–25 μL, supplied to the sample-application membrane and to the sample-collection membranes. The matrix has a preferred packing density between about 0.16 g/cm$^3$ and 4.0 g/cm$^3$. One exemplary strip material is a F-165-25A glass fiber filter available from Whatman, having a packing density of about 0.2 gm/cm$^3$ and a thickness of about 0.12 mm.

The device further includes four or more test pads 64, 66, 68, and 70, which are wettable, absorbent reaction test pads. Each test pad used in a particular assay contains analyte-dependent reagents effective to produce an analyte-dependent change in the pad which can be detected in a known manner, as described further below. All or any integral subset of the test pads may be employed in a particular assay.

Desirably, the test pads are porous polymer membranes, preferably having a thickness of about 100–150 μm and side dimensions of about 3 mm. The absorption volume of each pad is preferably between about 0.5–1.0 μL. In one embodiment, some or all of the reaction pads are asymmetric membranes; that is, membranes having a porosity gradient across the thickness of the membrane.

In one embodiment, test pad 64 is a HDL test pad containing reagents effective to produce a change in the pad in response to the presence of HDL. In another embodiment, the HDL test pad 64 is also a polymeric membrane, containing reagents for assaying HDL level. One exemplary strip material is a BTS-83 asymmetric polysulfone membrane available from Pall Corporation (East Hills, N.Y.). If desired, HDL assay reagents, such as peroxidase, may be immobilized to the test pad membrane, according to well known methods for enzyme immobilization. (See e.g. U.S. Pat. No. 4,999,287; U.S. Pat. No. 5,419,902; Blum, L. J. et al., *Anal. Lett.* 20(2):317–26 (1987); Kiang, S. W. et al., *Clin. Chem.* 22(8):1378–82 (1976); Guilbault, G. G., Ed., *Modern Monographs in Analytical Chemistry, Vol. 2: Analytical Uses of Immobilized Enzymes* (1984); Torchilin, V. P., *Progress in Clinical Biochemistry and Medicine*, Vol. 11: *Immobilized Enzymes in Medicine* (1991)).

A reagent pad 74 contacts the HDL test pad 64 and contains the chemicals for precipitation of non-HDL cholesterol. In one embodiment, the reagent pad is the same material as the HDL test pad, i.e. an asymmetric polysulfone membrane. In a preferred embodiment, reagent pad 74 is composed of a porous polymeric membrane, having pore sizes of about 1 μm or less. In the device shown in FIG. 1, reagent pad 74 consists of a single membrane, however, the invention also contemplates the use of multiple stacked membranes, i.e. up to about six, where at least one and preferably each membrane contains reagents for binding non-HDL lipoproteins.

The reagent pad preferably has a thickness of about 100–150 μm, side dimensions of about 3×6 mm, and an absorption volume of about 0.5–1.0 μL. It contains at least one reagent effective to selectively remove LDL and VLDL particles from the fluid sample. The reagent may be, for example, an antibody, or preferably a polyanionic LDL- and VLDL binding reagent. Such reagents, which are known in the art, include sulfonated polysaccharides, heparin, and phosphotungstate, in the presence or absence of a group II cation, such as $Mg^{2+}$, $Mn^{2+}$, or $Ca^{2+}$. A preferred reagent is a sulfonated polysaccharide, such as dextran sulfate, having a typical molecular weight of 50,000 to 500,000 daltons, optionally in combination with magnesium acetate or chloride, optionally buffered to maintain neutral pH. The reagent may be an immobilized reagent effective to bind, and remove from the fluid sample, non-HDL lipoproteins. The reagent pad is effective to entrap bound non-HDL lipoproteins within the reagent pad and prevent them from entering HDL test pad 64. In one embodiment, a reagent, such as catalase, which is effective to decompose any generated hydrogen peroxide that might diffuse downward from test pad 64, may be immobilized in reagent pad 74.

HDL test pad 64 and reagent pad 74 are adhered together using heat alone, as described in Example 6, or an acrylic acid copolymer that can be melted as a heat-activated adhesive, as described in Examples 1–3. The combined HDL test pad and reagent pad is called the assay pad.

Device 14 also includes a reaction bar 60, which is an elongate support, which may be transparent or have windows, e.g. window 76 (FIG. 2). The window(s) allow the test pads 64, 66, 68, and 70 to be viewed through the support. These windows may be transparent materials or simply openings in the support. The test pads and assay pad are attached to the reaction bar by a transparent or translucent adhesive material, by sonic welding, or other suitable bonding methods.

The reaction bar is mounted on support 15 by mounting means effective to (a) maintain the device in a sample-distribution position, wherein the test pads and assay pad are spaced apart from the sample distribution array, the sieving pad or the well, and to (b) transfer the device to a test position, where the test pads and assay pad are in fluid communication with the sample distribution array, the sieving pad and the well. The mounting means can also be used to break such fluid communication after a desired amount of sample has entered the assay pad and/or the test pads, and/or after a determined contact time, by transferring the device from the test position to a position in which the assay pad and/or the test pads are not in fluid communication with the sample well (which may be the same as the "sample-distribution" position). Such transferring can be controlled by monitoring the reflectance at the top surface of the test pads, which reflects extent of wetting, as described in co-owned U.S. Pat. No. 5,114,350, the content of which is incorporated by reference herein. Alternatively, when the absorption capacity and rate of sample uptake of the pad materials are known, the quantity of sample can be controlled with sufficient accuracy simply by using a predetermined contact time.

The mounting means can include, for example, a pair of resilient members, such as elastomeric blocks 71, 72, which act to bias the assay pad toward a non-transfer or sample-distribution position, at which the pads are spaced apart from the sample distribution array, the sieving pad, the capillary conduit or the sample well. By compression or release of the resilient members, fluid communication between the assay pad can be selectively established and separated, as shown in FIG. 3. The fluid communication may be via direct contact or through an intermediate element. The support blocks could be compressed by means of springs or a piston-like action. Alternatively, external mechanical devices could engage the main body 15 and/or reaction bar 60 and move one towards the other. Such devices may include conventional components such as clamps, pistons, stepper motors, worm gears, or the like. An exemplary system is the Cholestech LDX® Analyzer, a self-contained, automated analyzer advantageous for use with assay devices such as described herein.

In a further embodiment, the HDL test pad comprises a biosensor, as described, for example, in PCT Publication. No. WO 99/58966 (Dobson et al.), which is incorporated herein by reference. This document discloses a microscale biosensor device, comprising a conducting surface, a layer of dielectric material overlying the conducting surface, and a plurality of pores extending through the dielectric layer. Each of the pores contains a biopolymer in contact with the conducting surface, and can act as a microelectrode, converting a chemical response into an electrical signal. In use, a fluid containing an analyte to be assayed is applied to the pores so as to be in contact with the biopolymer. In the present HDL assay device, this is achieved when the HDL test pad 64 is in fluid communication with the sample, i.e. the test position as shown in FIG. 3.

The biopolymer within the microelectrode pores is typically an enzyme, such as, for the measurement of HDL-associated cholesterol, cholesterol oxidase. Cholesterol is oxidized by cholesterol oxidase to the corresponding ketone, liberating hydrogen peroxide, which can then be converted to water and oxygen by the enzyme peroxidase. Either oxygen or hydrogen peroxide can then be measured electrochemically. Electrochemical methods that may be used include amperometric methods, as in the Clark oxygen electrode, which measures current produced by reduction of oxygen or oxidation of hydrogen peroxide, or voltammetric methods. The use of cyclic voltammetry at microelectrodes has been described for measurement of various analytes (see e.g. R. J. Forster, *Chem. Soc. Rev.* 289–297 (1994)), such as dopamine (Pihel et al., *Anal. Chem.* 68(13):2084–9 (1996)) and fullerenes (Soucaze-Guillous et al., *Anal. Chem.* 65(6): 669–72 (1993)) as well as hydrogen peroxide (Horrocks et al., *Anal. Chem.* 65(24):3605–14 (1993); Nowall et al., *Electroanalysis* 9(2):102–9 (1997); Dequaire et al., *J. Am. Chem. Soc.* 124(2):240–53 (2002).

III. Preparation of the Assay Pad Using an Adhesive Layer

As seen in FIG. 1, in one embodiment, the assay pad is prepared by forming an adhesive layer 80 between the reagent pad 74 and the HDL test pad 64, as described in Examples 1–3. Joined by adhesive layer 80, reagent pad 74 and HDL test pad 64 form a composite structure referred to as the assay pad. It will be appreciated that the adhesive layer need only be sufficient to secure the opposing pads, e.g., by a peripheral seal, or can extend over the entire surfaces of the opposing pads.

The adhesive layer is preferably formed of an acrylic acid copolymer. The copolymer will typically, but not necessarily, have a melting point below the denaturing temperature of the HDL assay reagents used or below a temperature that is otherwise damaging to the HDL assay reagents. One exemplary copolymer is an Ethylene Acrylic Acid copolymer (EAA). EAA is available as different particle size dispersions from Michelman (Cincinnati Ohio, P/N MP 4990R with a melting point of about 75° C). One preferred particle size is 30–500 nm, with an average particle size of about 90 nm. Other polymers, including polyethylene glycol, polyethylene terephthalate, and polyvinyl alcohol, may also find use as the adhesive layer. These copolymers may be cross-linked and may further be copolymerized with a second, different polymer. In another embodiment, the adhesive layer is formed of a pressure sensitive adhesive or a wax emulsion. In yet another embodiment, the adhesive layer is formed of hot melt adhesives as described in U.S. Pat. No. 6,596,112, which is incorporated herein by reference. It will be appreciated that any substance may be used for the adhesive layer where the assay pad retains a suitable porosity for the sample to flow from the reagent pad to the HDL test pad.

The composite assay pad is typically prepared by dissolving the copolymer in a suitable solvent, often an aqueous-based solution. A layer of the copolymer emulsion or solution is applied to the reagent pad 74. Any suitable method for coating the pad may be utilized, including dipping the pads in the emulsion or solution, spray coating the pad or applying the polymer solution to the pad with a wick. The pad may be coated on one side only or on both sides. The pad is dried for a suitable time, i.e. for about 20 minutes at 50° C. The precipitating reagent is then dispensed onto the large pore (dull) side of the asymmetric membrane.

When the reagent pad and HDL test pad are both formed of an asymmetric membrane, the reagent pad and HDL test pad are oriented such that the small pore (shiny) side of the reagent pad contacts the open pore (dull) side of the HDL test pad.

The copolymer adhesive layer between the HDL test pad 64 and the reagent pad 74 is formed by applying heat and/or pressure to the coated reagent pad 74 and HDL test pad 64, whereby the copolymer forms a bond with the adjacent pad material. The pads may be heated using any suitable device that provides heat at the required temperature and pressure. A preferred temperature for heating the pads is about 80° C. Any suitable lamination machine may be used.

The concentration of copolymer on the reagent pad must be such that the assay pad retains porosity for the sample to flow from the reagent pad to the HDL test pad. Suitable concentrations of copolymer to provide adhesion are about 4.0% to about 10.0% emulsion. Preferred concentrations of the polymer coating are 4%, 5%, 6%, 7%, 8%, 9% and 10%. One preferred emulsion is a 5.5% EAA emulsion.

The HDL reagent may be dispensed onto HDL test pad 64 by any suitable method before or after adhering the test pad to the reagent pad. The HDL reagent is preferably dispensed onto the test pad after adhering the test pad to the reagent pad.

IV. Preparation of the Assay Pad Using Heat

In one embodiment, the assay pad is prepared by adhering the reagent pad 74 containing reagent to the HDL test pad 64 using heat applied at a temperature sufficient to at least partially melt at least one of the reagent pad or the HDL test pad, as described in Example 6. The reagent pad and HDL pad are heated above about 65° C. to about 220° C. as described in U.S. Pat. No. 6,596,112, which is incorporated herein by reference. In a preferred embodiment, when the reagent pad and HDL test pad are heated above about 165° C., the pads become adhered to each other. In other preferred embodiments, the reagent pad and HDL test pads are heated above about 93° C., 121° C., 148° C., 165° C., 200° C., or 205° C. The pads are oriented as described above. The HDL reagent is dispensed onto the HDL test pad before or after adhering the test pad to the reagent pad. In a preferred embodiment, the HDL reagent is dispensed onto the HDL test pad and/or the chemicals for precipitation of non-HDL cholesterol are dispensed onto the reagent pad after adhering the test pad to the reagent pad. In a particularly preferred embodiment, both the HDL reagent and the chemicals for precipitation are dispensed onto the HDL test pad and the reagent pad, respectively, after the test pad and the reagent pad are adhered together.

V. Dispensing Reagents onto Assay Pad Using Printing Process

In another embodiment, one or more reagents are applied to opposite sides of a pre-laminated membrane using a printing process that incorporates an engraved Gravure or Anilox cylinder. In this embodiment, less than a saturation volume of the HDL reagent and the precipitation reagent are used. By using non-saturating volumes, the reagents may be confined to their respective membranes. A volume of about 80 ml/1000 inch$^2$ is a typical saturating volume. Volumes in the range of 25 to 55 ml/1000 inch$^2$ of reagent are suitable, however, in one embodiment, 20 ml/1000 inch$^2$ reagent is used. The precipitation reagent may be applied before or after the HDL reagent. In other embodiments of this printing process, other reagents that contain two components that must be kept separate can be applied in like manner as described for the HDL reagents. Alternatively, a single reagent can be applied to a single unlaminated membrane.

VI. Assay Method

In operation, a blood sample is placed into well 16, and is imbibed through sieving pad 22, where large particulates, including red blood cells, are removed, and thence into the sample distribution array 26. In one embodiment, these steps take place while the device is in a "sample-distribution" stage, such that the assay pad is not in fluid communication with the sample distribution array, the sieving pad, the capillary conduit, or the sample well.

The plasma sample travels from sample-application membrane 28 to sample-collection membranes 30 and 32. When the plasma sample reaches sample-collection membranes, the device is adjusted to a test position, e.g. as shown in FIG. 3, preferably by moving reaction bar 60, to place the assay pad in fluid communication with the sample distribution array. In this position, sample fluid in the sample distribution array is drawn into the reagent pad by capillary flow. The sample fluid is further drawn into the HDL test pad(s) by capillary flow. The reaction bar is held at this position until a desired degree of wetting of the test pad(s) is achieved. The bar is then moved, if desired, to break fluid communication between the sample distribution array and the assay pad, when a desired amount of sample fluid has entered the assay pad(s), and/or after an appropriate contact time.

Prior to contacting the HDL test pad 64, sample plasma contacts a precipitating or binding reagent, which is contained in a separate reagent pad 74, such that non-HDL lipoproteins are bound to the respective carrier. The device is thus effective to remove non-HDL lipoproteins from the serum, while allowing passage of sample fluid containing liquid-phase HDL to HDL test pad 64 with these elements (e.g. FIG. 2). One advantage of this embodiment is that the sample distribution array and upstream elements do not contain non-HDL binding reagents; such reagents are present only in reagent pad 74. Therefore, the possibility of interference from these reagents, in assays of analytes other than HDL, is eliminated.

During operation, in embodiments such as illustrated in FIGS. 1–3, as sample fluid passes through the HDL assay path, comprising pads 74 and 64, its leading edge passes in an upward direction through pad 74, where non-HDL lipoproteins react and are entrapped, and directly to adjacent test pad 64, where HDL reacts with the assay reagents therein, for measurement of HDL-associated cholesterol. Further portions of sample continue to be in contact with pad 74 during this time, and proceed from pad 74 to pad 64 in a like manner, until the absorption capacity of pad 64 is reached. Accordingly, quantification of HDL-associated cholesterol in test pad 64 occurs concurrently with the binding reaction taking place in reagent pad 74. Preferably, the volume of sample fluid transferred to the HDL assay path (comprising pads 74 and 64) from the sample distribution matrix is equal to or greater than the absorption capacity of test pad 64, and less than or equal to the combined absorption capacity of test pad 64 and reagent pad 74.

In these embodiments, when the sample fluid contacts reagent pad 74 containing the binding reagents, the latter is in direct contact with HDL test pad 64, thus limiting the temporal contact of the blood sample with the binding reagents prior to the HDL assay reaction. Sample preparation and HDL evaluation are thus carried out in separate steps, where sample preparation includes, for example, filtering of cellular blood components and, optionally, temporary storage of the blood sample and adaptation of the blood sample to such test requirements or conditions as temperature, pressure and environmental atmosphere. Because the temporal contact of the blood sample with the different reagents is reduced, any chemical interference with the HDL evaluation is prevented. If desired, the assay can be interrupted for a desired time after the sample application and removal of cellular components, but prior to contact with binding reagents, e.g. to adjust the surrounding atmosphere or adapt the environmental temperature to support the testing. This is accomplished by maintaining the device in the sample-distribution position. To this end, the sample distribution matrix is designed to additionally serve as a reservoir, if needed.

The HDL test pad contains reagents for quantification of HDL-associated cholesterol. Preferably, these include cholesterol esterase, for releasing free cholesterol from HDL, cholesterol oxidase, for producing $H_2O_2$ by reaction with free cholesterol, peroxidase, and a coupled dye system which is converted, in the presence of peroxidase and $H_2O_2$, to a distinctively colored signal reaction product. The test pad may also comprise a biosensor effective to electrochemically quantify $H_2O_2$ and/or $O_2$, as described above.

The remaining test pads 66, 68, and 70 also contain assay reagents which produce a change in the pad, which can be detected optically, either visually or by a detector, in a known manner. In preferred embodiments of the current device and method, the non-HDL binding reagents are located in reagent pad 74, and not in the sample distribution array or sieving pad. In this embodiment, the possibility of interference from these reagents, in assays of analytes other than HDL, is eliminated.

Preferably, each of the test pads contains reagent components for producing $H_2O_2$ via reaction of the analyte with an enzyme; the $H_2O_2$ subsequently converts a substrate reagent to a colored signal reaction product, or is measured electrochemically, as described above. Enzymatic color reactions which employ a variety of substrate-specific oxidases, for enzymatic generation of $H_2O_2$, and subsequent oxidation of a dye to form a colored reaction product, are well known.

A device having four or more test pads can be used to simultaneously measure HDL cholesterol (HDL), glucose, total cholesterol (TC), triglyceride lipid (TRG), ALT, AST, BUN, and/or creatinine. Each pad contains the above-described common pathway components (peroxidase and a coupled dye system) such that generated $H_2O_2$ produces a distinctly colored signal reaction product. The total cholesterol test pad, which is exposed to serum without exposure to a precipitating or binding reagent, and the HDL test pads each include, in addition to the common pathway components, cholesterol esterase, for releasing esterified cholesterol in free-cholesterol form from serum lipoproteins, including HDL, LDL, and VLDL particles, and cholesterol oxidase, for producing $H_2O_2$ by reaction with free cholesterol in the sample fluid, as described above. The glucose assay pad includes glucose oxidase, in addition to the common-pathway components. The triglyceride pad includes, in addition to the common-pathway components, lipase, L-glycerol kinase, and L-glycerol-3-phosphate oxidase, for generating $H_2O_2$ from triglyceride, via the intermediate L-glycerol-3-phosphate. The serum sample drawn into the TRG pad is not exposed to precipitating or binding reagents, and thus contains all of the serum lipoproteins, so the TRG signal represents total serum triglycerides.

Reference standard pads may also be employed; see, for example, the system described in co-owned U.S. Pat. No. 5,114,350, which is incorporated herein by reference.

EXAMPLES

The following examples illustrate but are in no way intended to limit the invention.

Example 1

Preparation of HDL Test Pad

A BTS-83 polysulfone membrane was loaded with HDL reagent at a loading volume of 77 μl/in2 and dried for 20 minutes at 50° C. in a continuous roll process. Test pads containing the following HDL reagents were prepared: cholesterol oxidase 36.5 Units/ml, cholesterol esterase 215 Units/ml, peroxidase 200 Units/ml, 4-aminoantipyrine 1.88 mg/ml, and TOOS (3-[ethyl(3-methylphenyl)amino]-2-hydroxy propanesulfonic acid) 12.05 mg/ml. Lengths of e.g. 100 feet can be prepared in this manner and cut to fit the assay devices.

Example 2

Preparation of Reagent Pad with Binding Reagent

An aqueous reagent solution containing EAA dispersion at a concentration of 5.5% was applied to BTS-83 polysulfone membrane in a dip tank and dried for 20 minutes at 50° C. in a continuous roll process. Next, an aqueous reagent solution containing 1–5 mg/ml dextran sulfate (500,000 MW) and 35 mM Mg(OAc)$_2$ was dispensed onto the same membrane using a syringe pump to meter reagent onto one surface of the membrane. Lengths of e.g. 100 feet can be prepared in this manner and cut to fit assay devices.

Example 3

Preparation of Assay Pad

A HDL test pad and a reagent pad were prepared according to Examples 1 and 2, respectively. The pads were oriented with the layers having the shiny side of the reagent pad (small pore size) contacting the dull or open pore side of the HDL test pad. The two membranes were passed through a lamination machine that heated the membranes to 80° C. for 20 seconds in a continuous roll process.

Example 4

Representative Assay Procedure

A typical assay was carried out in an LDX® analyzer, using an assay pad, prepared essentially as described in Example 3. Sections of the adhered pads were hand cut to reaction membrane size and attached to the reaction bar. Alternatively, laminated assay pads can be applied to reaction bars in a continuous roll process using ultrasonic welding. A serum sample was loaded in the sample well. After sample distribution, the reaction bar was contacted with the adhered pads for approximately 4 seconds, a time sufficient to transfer enough serum to fill the HDL test pad, after which the bar was returned to its original position. The color was allowed to develop for 3 minutes and the reflectance was monitored by the LDX® analyzer.

Example 5

Acrylic Acid Copolymer Concentration on Reagent Pad

The concentration of EAA on the reagent pad was varied to determine porosity of the membrane. The reagent pad was prepared essentially according to Example 2. Serial dilutions of EAA were applied to the reagent pad starting with a 20% solution. The reagent pads were adhered according to Example 3 to a HDL test pad. The dull side of the reagent pad was tested with a dilute aqueous solution of Evan's blue to determine penetration and/or diffusion of the colored solution through the reagent pad and into the HDL test pad. The highest concentration of EAA that allowed ready penetration and/or diffusion of the solution was about 10% EAA.

Example 6

Preparation of Assay Pad Using Heat

Two layers of BTS 83, without any reagents applied, are laminated together in a continues roll process. The orientation of membranes is as described for Example 3. An aqueous solution of Dextran sulfate (50,000 MW) and Mg(OAc)$_2$ is coated onto the open pore side of the laminate using a standard gravure coater. The gravure coater is selected to dispense a non-saturating volume of reagent onto a single layer of the laminate. Following drying, the HDL reagent is applied to the opposite membrane in a similar manner. The reagents are concentrated from the levels shown in Example 1 and 2 to compensate for the reduced volume being applied.

It is claimed:

1. An assay device for measuring serum cholesterol associated with high-density lipoproteins (HDL) in a blood fluid sample containing lipoproteins other than HDLs of the type including a sample distribution array effective to distribute a blood fluid sample from a sample application region to one or more sample collection regions, the device comprising:
    a HDL test pad in which HDL concentration can be assayed being spaced apart from said array, said HDL test pad being affixed to a mounting means; and
    a reagent pad containing a binding reagent effective to selectively bind and remove non-HDLs from the fluid sample;
    wherein said HDL test pad and said reagent pad are joined by a bond selected from the group consisting of a heat formed bond and heat activated adhesive bond;
    wherein said mounting means are effective (i) to maintain the device in a sample-distribution position, wherein said joined HDL test pad and reagent pad are spaced apart from said array, and (ii) to transfer said device to a test position, whereby the joined HDL test pad and reagent pad are in contact with said array.

2. The device of claim 1, wherein at least one of said HDL test pad or said reagent pad is composed of a polysulfone layer.

3. The device of claim 1, further comprising a sieving pad in fluid communication with said sample application region and said one or more sample collection regions effective to remove cellular components from the blood fluid sample prior to the sample contacting said sample distribution array.

4. The device of claim 3, further comprising a cassette body for containing said sieving pad, said cassette body comprising a well for containing said blood fluid sample and in fluid communication with said sieving pad.

5. The device of claim 4, further comprising a reaction bar comprising mounting means effective to attach said reaction bar to said cassette body.

6. The device of claim 1, wherein said reagent comprises a binding polyanionic reagent.

7. The device of claim 6, wherein said binding polyanionic reagent includes a sulfonated polysaccharide.

8. The device of claim 1, wherein said HDL test pad contains reagents which produce a detectable change in the presence of HDL cholesterol.

9. The device of claim 8, wherein said change can be detected optically.

10. The device of claim 1, wherein said HDL test pad comprises a biosensor.

11. The device of claim 10, wherein said biosensor is effective to electrochemically measure production of oxygen or hydrogen peroxide.

12. The device of claim 1, wherein said bond extends along the periphery of at least one of the HDL test pad and the reagent pad.

13. The device of claim 1, wherein said bond extends along the entire surface of at least one of the HOL test pad and the reagent pad.

14. The assay device of claim 1, wherein said heat activated adhesive bond is an acrylic acid copolymer adhesive bond.

15. The device of claim 14, wherein said acrylic acid copolymer is ethylene acrylic acid copolymer.

16. A method of preparing a device suitable for measuring serum cholesterol comprising:
   providing a reagent pad and an HDL test pad, wherein at least the reagent pad is formed of an asymmetric polysulfone membrane having a small pore side and an open pore side;
   heating to adhere said HDL test pad and said reagent pad; and
   applying (i) HDL test reagents to said HDL test pad, and (ii) a reagent effective to selectively bind and remove non-HDLs from a fluid sample to said reagent pad to form said device.

17. The method of claim 16, wherein said heating is at a temperature above 165° C.

18. The method of claim 16, wherein each of said HDL test pad and said reagent pad are formed of an asymmetric polysulfone membrane having a small pore side and an open pore side, said method further comprising:
   before said heating, orienting the reagent pad with the HDL test pad such that the small pore side of the reagent pad contacts the open pore side of the HDL test pad.

19. The method of claim 16, wherein the periphery of at least one of the HDL test pad and the reagent pad is heated.

20. The method of claim 16, wherein the entire surface of at least one of the HDL test pad and the reagent pad is heated.

21. A method of preparing a device suitable for measuring serum cholesterol comprising:
   coating a reagent pad with heat activated adhesive;
   applying (i) HDL test reagents to an HDL test pad, and (ii) a reagent effective to selectively bind and remove non-HDLs from a fluid sample to said reagent pad;
   heating to adhere said HDL test pad and said reagent pad to form said device.

22. The method of claim 21, further comprising the step of drying said reagent pad after said coating step.

23. The method of claim 21, wherein each of said HDL test pad and reagent pad have a small pore side and an open pore side; further comprising the step of orienting the HDL test pad and the reagent pad such that the small pore side of the reagent pad faces the open pore side of the HDL test pad.

24. The method of claim 21, wherein said heating step comprises applying a temperature of between 75° and 90° C.

25. The method of claim 21, wherein the periphery of the reagent pad is coated with the heat activated adhesive.

26. The method of claim 21, wherein the entire surface of the reagent pad is coated with the heat activated adhesive.

27. The method of claim 21, wherein said heat activated adhesive is an acrylic acid copolymer adhesive.

28. The method of claim 27, wherein said acrylic acid copolymer is ethylene acrylic acid copolymer.

29. The method of claim 28, wherein the ethylene acrylic acid copolymer is about 4.0% to about 10.0% emulsion.

30. A method of measuring serum cholesterol associated with high-density lipoproteins (HDL) in a blood fluid sample containing lipoproteins other than HDLs, comprising:
   contacting the sample with a sample reservoir through which the sample is distributed to one or more sample collection sites;
   bringing into contact with such a sample collection site a laminate comprising (i) a reagent pad containing a reagent effective to selectively bind and remove non-HDLs from the fluid sample, and (ii) an HDL test pad having a detectable indicator of HDL cholesterol;
   wherein said blood fluid sample passes through said laminate by capillary action and/or gravity through said laminate to permit measurement of HDL concentration; and
   measuring the level of HDL cholesterol in said sample by detection at said HDL test pad.

31. The method of claim 30, wherein contact between said laminate and said sample collection site is broken when a desired amount of sample has been transferred.

32. The method of claim 30, wherein said reagent comprises a sulfonated polysaccharide.

33. The method of claim 30, wherein at least one of said HDL test pad or said reagent pad comprises a porous polymeric membrane.

34. The method of claim 30, wherein said reagent pad comprises multiple stacked layers, at least one of which contains a reagent effective to bind non-HDLs.

35. The method of claim 30, wherein said measurement of HDL concentration is via optical detection.

36. The method of claim 30, wherein said HDL test pad comprises a biosensor.

37. The method of claim 36, wherein said biosensor is effective to electrochemically measure production of oxygen or hydrogen peroxide.

* * * * *